United States Patent [19]

Carr et al.

[11] 4,284,636
[45] Aug. 18, 1981

[54] CINNAMOYLPIPERIDINOBUTYROPHE-
NONE ANTIPSYCHOTIC AGENTS

[75] Inventors: Albert A. Carr; Robert A. Farr, both of Cincinnati, Ohio

[73] Assignee: Richardson-Merrell Inc., Wilton, Conn.

[21] Appl. No.: 72,498

[22] Filed: Sep. 4, 1979

[51] Int. Cl.³ .............. C07D 211/70; C07D 405/06; A61K 31/445
[52] U.S. Cl. .................. 424/267; 542/438; 546/207; 546/225
[58] Field of Search ............. 424/267; 542/438; 546/207, 225

[56] References Cited

U.S. PATENT DOCUMENTS

| | | | |
|---|---|---|---|
| 3,080,372 | 3/1963 | Janssen | 546/225 |
| 3,484,446 | 12/1969 | Biel et al. | 542/207 |
| 3,580,910 | 5/1971 | Thiel et al. | 424/267 |
| 3,590,041 | 6/1971 | Kleeman et al. | 424/267 |
| 3,646,014 | 2/1972 | Bader et al. | 546/207 |
| 3,689,492 | 9/1972 | Schroeder et al. | 546/225 |
| 3,799,932 | 3/1904 | Yamamoto et al. | 424/267 |
| 3,816,433 | 6/1974 | Hernestam et al. | 424/267 |
| 4,101,662 | 7/1978 | Ward et al. | 424/267 |

FOREIGN PATENT DOCUMENTS 516557 1/1972 Switzerland .

OTHER PUBLICATIONS

Krauch et al., Organic Name Reactions, John Wiley & Sons, N.Y., N.Y., 1964, p. 6–9.

Primary Examiner—Arthur P. Demers
Attorney, Agent, or Firm—John J. Kolano; Raymond A. McDonald; William J. Stein

[57] ABSTRACT

Cinnamoylpiperidinobutyrophenone derivatives and pharmaceutically acceptable salts thereof of the following general structure:

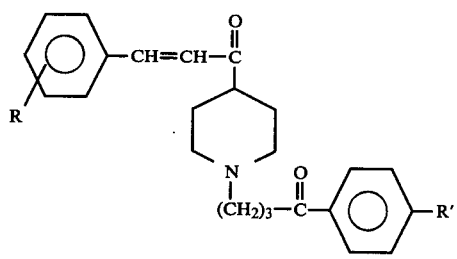

wherein R is hydrogen, alkyl, alkoxy, halogen or trifluoromethyl; and R' is hydrogen or halogen; are useful as antipsychotic agents. The novel compounds are produced by aldol condensation of a benzaldehyde with a protected 4-(4-acetyl-1-piperidino)-butyrophenone.

11 Claims, No Drawings

CINNAMOYLPIPERIDINOBUTYROPHENONE ANTIPSYCHOTIC AGENTS

BACKGROUND OF THE INVENTION

This invention relates to cinnamoylpiperidinobutyrophenone derivatives and pharmaceutically acceptable salts thereof which are useful as antipsychotic agents. More particularly, it relates to 4-(4-cinnamoyl-1-piperidino)-butyrophenones and to intermediates and processes for preparing the same.

Related 4-aroyl-1-piperidinobutyrophenones are known, for example, in U.S. Pat. Nos. 3,852,455, 3,888,867 and 4,101,662, Netherlands Pat. No. 7,409,752, and Costall et al, *Psycopharmacologia*, 32(2), 161-170 (1973).

SUMMARY OF THE INVENTION

The cinnamoylpiperidinobutyrophenones of this invention have the general Formula I

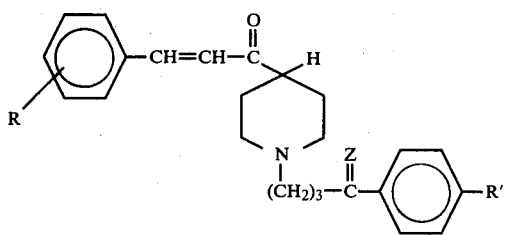

wherein Z is an oxygen atom; R is hydrogen, alkyl, alkoxy, halogen or trifluoromethyl; and R' is hydrogen or halogen. Pharmaceutically acceptable acid addition salts of the above compounds are also included within the scope of the invention, as are pharmaceutical compositions comprising them and methods for preparing and using them.

The invention further includes compounds having the general Formulae I and II

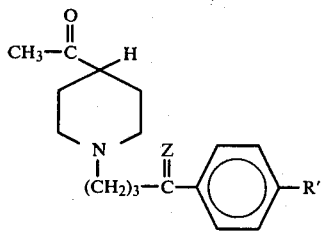

wherein R and R' are as defined for Formula I, and Z is a dialkyl or alkylene ketal function, which are key intermediates in the preparation of compounds of Formula I (Z=O).

DETAILED DESCRIPTION OF THE INVENTION

In the compounds of Formula I, the substituent R may be hydrogen, trifluoromethyl, alkyl, especially $C_{1-4}$ alkyl, such as methyl, ethyl, n-propyl, isopropyl, n-butyl, isobutyl, sec-butyl and tert-butyl, alkoxy, especially $C_{1-4}$ alkoxy, such as methoxy, ethoxy, n-propoxy, isopropoxy, n-butoxy, isobutoxy, sec-butoxy and tert-butoxy, or a halogen atom such as fluorine, chlorine or bromine. The R substituent may be in the ortho, meta or para position on the phenyl radical.

The substituent R' may be a hydrogen atom or a halogen atom such as fluorine, chlorine or bromine, especially fluorine.

The substituent Z is an oxygen atom or a dialkyl or alkylene ketal function, e.g., dialkoxy of 1-8, preferably 1-3 carbon atoms in each alkoxy group, e.g., methoxy or ethoxy, and alkylenedioxy of 2-8, preferably 2-4 carbon atoms, having 2 or 3 carbon atoms in the chain between the oxygen atoms, e.g., ethylenedioxy, 1,2-propylenedioxy and trimethylenedioxy.

The double bond of the cinnamoyl group may be cis or trans, or a mixture of geometric isomers. The compounds with a trans (E) double bond are preferred.

The preferred compounds of this invention are compounds of Formula I wherein Z is an oxygen atom; R is hydrogen, p-fluoro and p-chloro; and R' is a fluorine atom; and having a trans (E) double bond.

The invention also includes the pharmaceutically acceptable acid addition salts of the compounds of the hereinbefore set forth formulae, such as those salts with inorganic acids such as, for example, hydrochloric, hydrobromic, sulphuric, phosphoric acids and the like and with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic acid and the like.

Illustrative of compounds of this invention are, for example, 4-(4-cinnamoyl-1-piperidino)-p-fluorobutyrophenone, 4-(4-p-fluorocinnamoyl-1-piperidino)-p-fluorobutyrophenone, and 4-(4-p-chlorocinnamoyl-1-piperidino)-p-fluorobutyrophenone, especially the trans (E) isomers thereof.

The compounds of Formula I (Z=O) and their acid addition salts are antipsychotic agents. They can be administered in the form of pharmaceutical preparations in unit dosages suitable for oral or parenteral administration. The pharmaceutical preparations may be administered in solid form, for example, capsules, pills, or tablets, or in liquid form, either form optionally containing, in addition to the active compounds, a significant quantity of a pharmaceutically acceptable carrier. The compounds may be administered to animals, including rats, mice, dogs, cats, horses, pigs, cows, sheep, birds, warm-blooded animals and mammals, and humans. The quantity of the active compound of Formula I (Z=O) in the unit dosage can vary over a wide range, for example, to provide about 0.01-20 mg/kg of body weight of the treated subject per dose to achieve the desired antipsychotic effect. The effect can be obtained, for example, by consumption of from one to three 1-50 mg tablets taken 1-4 times daily.

The compounds of this invention can be used in the management of manifestations of psychotic disorders and can thus be used in a manner similar to haloperidol, a known antipsychotic agent.

Their effectiveness as antipsychotic agents is indicated by significant blocking of amphetamine grouped toxicity with low liability from extrapyramidal side effects, using standard test conditions.

The following reaction scheme illustrates a method of preparing compounds according to the invention:

SCHEME 1:

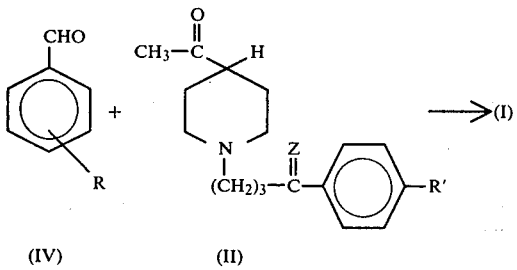

wherein R, R' and Z as ketal are as defined hereinbefore. The aldol condensation reaction between a benzaldehyde and a 4-acetyl-1-piperidino-butyrophenone ketal is normally carried out in the presence of a mild base, such as piperidinium acetate, in a suitable solvent. The reaction is generally effected over the course of about 4 hours to about three days, advantageously at an elevated temperature such as the boiling point of the solvent. Suitable solvents include hydrocarbons, such as benzene and toluene. The cooled reaction mixture is partitioned between an organic and aqueous phase, and the crude ketal of Formula I (Z=ketal) is recovered from the organic phase after removal of the solvents.

Hydrolysis of the ketal is normally effected by stirring at 0°–40° C. in a mixture of water and an organic solvent such as tetrahydrofuran (THF) or a lower (e.g., $C_{1-4}$) alcohol, in the presence of a strong acid such as hydrochloric, p-toluenesulfonic (HOTs) or perchloric acid. Neutralization and extraction into an organic phase, washing with water and brine, drying over magnesium sulfate, and concentration yields a crude product of Formula I (Z=O). Further purification is typically effected by chromatography followed by formation of a salt, such as the hydrochloride, and recrystallization.

The novel 4-(4-acetyl-1-piperidino)-butyrophenone ketals II used in the reaction of SCHEME 1 may be prepared as follows:

SCHEME 2:

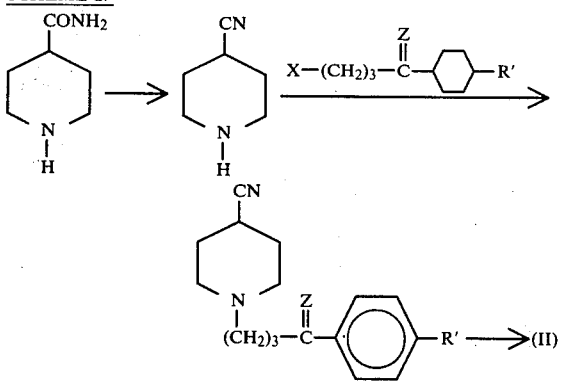

wherein R' and Z (ketal) are as defined hereinbefore, and X is a reactive halogen such as bromine, chlorine, or iodine or an equivalent reactive leaving group. Commercially available piperidine-4-carboxamide is converted to 4-cyanopiperidine, typically by reaction with trifluoroacetic anhydride, followed by hydrolysis of the resultant 4-cyano-1-trifluoroacetylpiperidine using alcoholic carbonate at from 20° C. to the temperature of reflux. Alkylation with a 4-halobutyrophenone ketal, typically the ethyelenedioxy derivative, is normally carried out in the presence of an acid acceptor, such as, for example, sodium or potassium carbonate or bicarbonate, and is optionally catalyzed by a small amount of potassium iodide, in a suitable solvent. The reaction is generally effected over the course of about four hours to about three days, advantageously at an elevated temperature such as the boiling point of the solvent. Suitable solvents include aromatic hydrocarbons, such as toluene, xylene or chlorobenzene, ketones such as methyl isobutyl ketone, or lower alcohols such as ethanol, propanol, butanol and the like. Preferably, the reaction is run using potassium carbonate in n-butanol at reflux for five hours. The cooled reaction mixture is partitioned between an organic and aqueous phase and the product ketal isolated from the organic phase after removal of solvents. Conversion of the cyano group to an acetyl group is easily accomplished by addition of a methyl Grignard reagent, followed by hydrolysis. The reaction is typically effected by adding a benzene solution of the nitrile to an ethereal solution of the Grignard reagent, while distilling off the ether, quenching with water, partitioning between an organic and aqueous phase, and isolating the product from the organic phase after evaporation of the solvents. The ketone-ketal II is suitable for use in the aldol condensation of SCHEME 1.

Preparation of the 4-halobutyrophenone ketals used in the reaction of SCHEME 2 is effected by reacting an appropriate glycol in benzene or toluene with a commercially available 4-halobutyrophenone, catalyzed by p-toluenesulfonic acid (HOTs) with azeotropic water removal, typically by use of a Dean-Stark trap. Reaction time varies from 12 to 72 hours, generally 40–48 hours. Alternatively, the 4-halobutyrophenone ketal can be prepared by reaction with an alcohol and one equivalent of the corresponding trialkyl orthoformate in the presence of an acid catalyst such as HOTs.

EXAMPLES

The following examples are illustrative of the invention.

EXAMPLE 1

4-(4-Cyano-1-piperidino)-p-fluorobutyrophenone ethylene ketal 4-cyanopiperidine is prepared by reacting 130 g (1.02 moles) of piperidine-4-carboxamide (Aldrich Chemical Company) and 454 g (2.16 moles) of trifluoroacetic anhydride, and heating at reflux for 19 hours. Trifluoroacetic anhydride and trifluoroacetic acid are removed in vacuo, and the residual 4-cyano-1-trifluoroacetylpiperidine is added slowly to 345 g (2.5 moles) of potassium carbonate in 650 ml water and 1500 ml methanol. The reaction mixture is heated until most of the methanol boils off, 500 ml of benzene is added and the solution is heated until the vapor reaches a temperature of 85° C. The cooled reaction mixture is saturated with NaCl, extracted with methylene chloride, and the extracts dried over sodium sulfate and concentrated. The residue is dissolved in ether, filtered, concentrated in vacuo and distilled to give 30.2 g of 4-cyanopiperidine, b.p. 115°–116° C. at aspirator pressure.

A mixture of 11.1 g (0.10 mole) of 4-cyanopiperidine, 24.8 g (0.10 mole) of the ethylene ketal of 4-chloro-p-fluorobenzophenone (prepared by ketalizing the ketone with ethylene glycol in benzene/HOTs using a Dean- Stark trap) and 21 g (0.152 mole) of potassium carbonate in 200 ml of n-butanol are refluxed for 17 hours. Water is added to the cooled reaction mixture, the aqueous layer saturated with NaCl and the organic layer diluted with ether. The aqueous layer is extracted with benzene and the combined organic layers dried over magnesium sulfate and concentrated to give 31.5 g of the ethylene ketal of 4-(4-cyano-1-piperidino)-p-fluorobutyrophenone as a pale yellow oil. The isolated product is suitable for use in the Grignard reaction of EXAMPLE 2.

EXAMPLE 2

4-(4-Acetyl-1-piperidino)-p-fluorobutyrophenone ethylene ketal (II, R'=F, Z=OCH₂CH₂O)

A solution of 15.9 g (50.0 mmoles) of the cyano-ketal produced in EXAMPLE 1 in 125 ml of benzene is added dropwise to a solution of methyl magnesium iodide (100 mmoles) prepared from 2.43 g of magnesium and 6.23 ml methyl iodide, in 125 ml ether, while simultaneously distilling off the ether. 10 ml of dry THF are added, and the mixture refluxed for 16 hours, quenched with water and partitioned between aqueous alkali and ether/benzene/methylene chloride. The organic phase is filtered, the aqueous phase reextracted with ether, and the combined organic extracts washed with water, brine, dried over sodium sulfate and concentrated in vacuo to give 15.0 g of the desired ketal-ketone II as an oil which is suitable for use in the condensation reaction of EXAMPLE 3.

EXAMPLE 3

(E)-4-(4-p-Fluorocinnamoyl-1-piperidino)-p-fluorobutyrophenone (I, Z=O, R=p-F, R'=F) (hydrochloride salt)

A solution of 3.71 g (11.1 mmoles) of the ketone-ketal produced in EXAMPLE 2, 1.54 g (12.4 mmoles) of p-fluorobenzaldehyde, in 25 ml of benzene, containing 1.0 ml (10.1 mmoles) of piperidine and 0.1 ml (1.8 mmoles) of glacial acetic acid, is fitted with a Dean-Stark trap for separation of water, and heated at reflux for 24 hours. After 2 hours, 0.56 ml (10 mmoles) of glacial acetic acid is added. The cooled reaction mixture is concentrated in vacuo to give the intermediate ketal I(Z=—OCH₂CH₂O—), which is taken up in 50 ml of THF and 25 ml of water, treated with a solution of 6 ml 70% perchloric acid and 10 ml water, warmed slightly and stirred at room temperature for 4 hours. The hydrolysis product is poured into water and cyclohexane/ether, resulting in separation of product as a brown gum. The gum and the aqueous layer are made basic with dilute alkali and a little methanol, and extracted with ether. The ether extracts are washed with aqueous alkali, brine, dried over magnesium sulfate, and concentrated in vacuo to give the desired crude product. Recrystallization from cyclohexane/benzene, cyclohexane alone, solution in hot ethanol and formation of the hydrochloride salt, which is recrystallized from butanone/methanol gives the pure product, m.p. 208°–210.5° C. as yellow flakes.

EXAMPLE 4

(E)-4-(4-p-Chlorocinnamoyl-1-piperidino)-p-fluorobutyrophenone (I, Z=O, R=p-Cl, R'=F) (hydrochloride salt)

By the procedure described in EXAMPLE 3, using p-chlorobenzaldehyde, the desired hydrochloride salt is obtained. Recrystallization from butanone/methanol gives the pure product as pale yellow needles, m.p. 227.5°–230.5° C.

EXAMPLE 5

(E)-4-(4-Cinnamoyl-1-piperidino)-p-fluorobutyrophenone (I, Z=O, R=H, R'=F) (hydrochloride salt)

By the procedure described in EXAMPLE 3, using benzaldehyde, the desired hydrochloride salt is obtained. Recrystallization from butanone/methanol gives the pure product as white crystals, m.p. 205°–207.5° C.

EXAMPLE 6

Tablet Formulation

Exemplary of a representative tablet formulation of an active compound of this invention, there may be mentioned the following:

|     |                                                                  | Per Tablet |    |
| --- | ---------------------------------------------------------------- | ---------- | -- |
| (a) | 4-(4-p-fluorocinnamoyl-1-piperidino)-p-fluorobutyrophenone hydrochloride | 25.0 | mg |
| (b) | Wheat starch                                                     | 3.5        | mg |
| (c) | Lactose                                                          | 10.0       | mg |
| (d) | Magnesium stearate                                               | 0.5        | mg |

A granulation obtained upon mixing lactose with a portion of the starch and granulated starch paste made from the remainder of the starch is dried, screened and mixed with the active ingredient (a) and the magnesium stearate. The mixture is compressed into tablets weighing 39.0 mg each.

We claim:

1. A compound of the formula

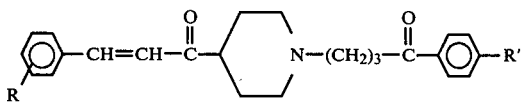

wherein R is hydrogen, $C_{1-4}$ alkyl, $C_{1-4}$ alkoxy, fluorine, chlorine, bromine, or trifluoromethyl; and R' is hydrogen, fluorine, chlorine or bromine; and pharmaceutically acceptable acid addition salts thereof.

2. A compound of claim 1, wherein R' is fluorine.

3. The compound of claim 1, which is 4-(4-cinnamoyl-1-piperidino)-p-fluorobutyrophenone, and pharmaceutically acceptable acid addition salts thereof.

4. The compound of claim 1, which is 4-(4-p-fluorocinnamoyl-1-piperidino)-p-fluorobutyrophenone, and pharmaceutically acceptable acid addition salts thereof.

5. The compound of claim 1, which is 4-(4-p-chlorocinnamoyl-1-piperidino)-p-fluorobutyrophenone, and pharmaceutically acceptable acid addition salts thereof.

6. A compound of claim 1, having the formula

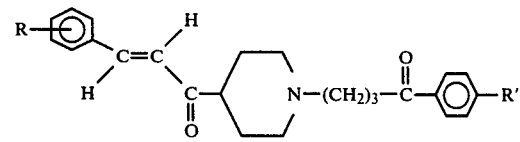

wherein R and R' are as defined therein; and pharmaceutically acceptable acid addition salts thereof.

7. The compound of claim 6, which is (E)-4-(4-cinnamoyl-1-piperidino)-p-fluorobutyrophenone, and pharmaceutically acceptable acid addition salts thereof.

8. The compound of claim 6, which is (E)-4-(4-p-fluorocinnamoyl-1-piperidino)-p-fluorobutyrophenone, and pharmaceutically acceptable acid addition salts thereof.

9. The compound of claim 6, which is (E)-4-(4-p-chlorocinnamoyl-1-piperidino)-p-fluorobutyrophenone, and pharmaceutically acceptable acid addition salts thereof.

10. A pharmaceutical composition comprising in unit dosage form from about 1 mg to 50 mg of a compound of the formula

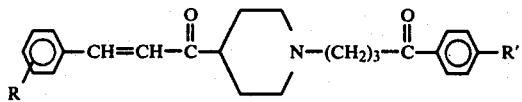

wherein R is hydrogen, $C_{1-4}$ alkyl, $C_{1-4}$ alkoxy, fluorine, chlorine, bromine or trifluoromethyl; and R' is hydrogen, fluorine, chlorine or bromine; and a significant amount of a pharmaceutically acceptable carrier.

11. A compound of the formula

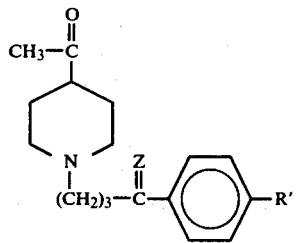

wherein R' is hydrogen, fluorine, chlorine or bromine; and Z is a ketal function selected from dialkoxy of 1–8 carbon atoms in each alkoxy group and alkylenedioxy of 2–8 carbon atoms and 2–3 carbon atoms in the chain.

* * * * *